US011457875B2

(12) United States Patent
Yamaoka et al.

(10) Patent No.: US 11,457,875 B2
(45) Date of Patent: Oct. 4, 2022

(54) EVENT PREDICTION SYSTEM, SENSOR SIGNAL PROCESSING SYSTEM, EVENT PREDICTION METHOD, AND NON-TRANSITORY STORAGE MEDIUM

(71) Applicant: PANASONIC INTELLECTUAL PROPERTY CORPORATION OF AMERICA, Torrance, CA (US)

(72) Inventors: Masaru Yamaoka, Osaka (JP); Toshiaki Tanaka, Hyogo (JP); Kenji Masuda, Osaka (JP); Atsushi Takahashi, Nara (JP); Hidehiko Ichikawa, Gunma (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 839 days.

(21) Appl. No.: 16/289,082

(22) Filed: Feb. 28, 2019

(65) Prior Publication Data

US 2019/0274634 A1  Sep. 12, 2019

(30) Foreign Application Priority Data

Mar. 8, 2018 (JP) .............................. JP2018-042433
Mar. 8, 2018 (JP) .............................. JP2018-042435
Nov. 30, 2018 (JP) .............................. JP2018-226053

(51) Int. Cl.
*A61B 5/11* (2006.01)
*G08B 21/04* (2006.01)
(Continued)

(52) U.S. Cl.
CPC .......... *A61B 5/7275* (2013.01); *A61B 5/1113* (2013.01); *A61B 5/1126* (2013.01);
(Continued)

(58) Field of Classification Search
CPC ............... A61B 5/7275; A61B 5/1113; A61B 5/6889; G08B 21/02; G08B 21/0211;
(Continued)

(56) References Cited

U.S. PATENT DOCUMENTS 9,808,205 B2 * 11/2017 Koyama ................ A61B 5/742
10,548,512 B2 * 2/2020 Hausdorff ............ A61B 5/6831
11,313,962 B2 * 4/2022 Yamaoka ................ G01S 13/56
2010/0204550 A1 8/2010 Heneghan et al.
2015/0134263 A1 * 5/2015 Maeno ..................... A61B 5/05
702/19

(Continued)

FOREIGN PATENT DOCUMENTS

JP 2012-075861 4/2012
JP 2013-097670 5/2013
(Continued)

OTHER PUBLICATIONS

Official Communication Received in Japanese Patent Application No. 2018-226053, dated Jun. 21, 2022.

*Primary Examiner* — John A Tweel, Jr.
(74) *Attorney, Agent, or Firm* — Greenblum & Bernstein, P.L.C.

(57) ABSTRACT

An event prediction system according to an aspect includes an acquisition unit and a symptom detection unit. The acquisition unit acquires body movement data about a subject's body movement from a measuring device that outputs the body movement data. The symptom detection unit makes, based on a subset, acquired during a past reference period, of the body movement data, a decision about whether or not there are any symptoms of an onset of a particular event related to the subject.

12 Claims, 4 Drawing Sheets

(51) Int. Cl.
*A61B 5/00* (2006.01)
*G08B 21/02* (2006.01)
*A61B 5/05* (2021.01)

(52) U.S. Cl.
CPC .......... *A61B 5/4088* (2013.01); *A61B 5/6889* (2013.01); *A61B 5/7278* (2013.01); *G08B 21/02* (2013.01); *G08B 21/0211* (2013.01); *G08B 21/043* (2013.01); *G08B 21/0415* (2013.01); *G08B 21/0423* (2013.01); *G08B 21/0469* (2013.01); *A61B 5/05* (2013.01)

(58) Field of Classification Search
CPC ............ G08B 21/0415; G08B 21/0423; G08B 21/043; G08B 21/0469
See application file for complete search history.

(56) References Cited

U.S. PATENT DOCUMENTS

| 2016/0077123 | A1* | 3/2016 | Kagaya | A61B 5/6889 |
| | | | | 702/150 |
| 2016/0328533 | A1 | 11/2016 | Kawai et al. | |
| 2020/0064456 | A1* | 2/2020 | Xu | G01S 13/765 |
| 2020/0408875 | A1* | 12/2020 | Mai | H04W 24/06 |

FOREIGN PATENT DOCUMENTS

| JP | 2016-047110 | 4/2016 |
| JP | 2017-000484 | 1/2017 |
| JP | 2017-094188 | 6/2017 |
| WO | 2015/107710 | 7/2015 |

* cited by examiner

EVENT PREDICTION SYSTEM, SENSOR SIGNAL PROCESSING SYSTEM, EVENT PREDICTION METHOD, AND NON-TRANSITORY STORAGE MEDIUM

CROSS-REFERENCE TO RELATED APPLICATIONS

This application claims the benefit of foreign priority to Japanese Patent Application No. 2018-42433 and No. 2018-42435 filed on Mar. 8, 2018 and Japanese Patent Application No. 2018-226053 filed on Nov. 30, 2018, the entire contents of which are hereby incorporated by reference.

TECHNICAL FIELD

The present disclosure generally relates to an event prediction system, a sensor signal processing system, an event prediction method, and a non-transitory storage medium, and more particularly relates to an event prediction system, a sensor signal processing system, an event prediction method, and a non-transitory storage medium, all of which use body movement data about the subject's body movement.

BACKGROUND ART

JP 2017-484 A (hereinafter referred to as "D1") discloses a noncontact activity sensor (sensor processing system), which includes a Doppler sensor (measuring unit), a distance sensor, and a processor. The processor calculates the volume of activity of a subject, falling within the sensing range of the sensor (air-conditioned space), based on the amplitude and/or frequency of a detection signal of the Doppler sensor and a detection signal of the distance sensor. D1 describes that air conditioning control is performed based on the volume of activity thus calculated.

D1 also teaches evaluating the user's fitness level based on the volume of activity detected. For example, based on a variation in the volume of the user's activity, the activity sensor of D1 detects any health problems with the user or checks his or her fitness level for any injuries, pains, or sufferings.

However, the activity sensor of D1 is basically designed for the purpose of air conditioning control, and may be used just to diagnose the user's current condition. In other words, the activity sensor of D1 is not configured to use the volume of activity detected for other purposes.

SUMMARY

The present disclosure provides an event prediction system, a sensor signal processing system, an event prediction method, and a non-transitory storage medium, all of which are configured or designed to make a decision about event symptoms of the onset of any particular event related to the subject.

An event prediction system according to an aspect of the present disclosure includes an acquisition unit and a symptom detection unit. The acquisition unit acquires body movement data about a subject's body movement from a measuring device that outputs the body movement data. The symptom detection unit makes, based on a subset, acquired during a past reference period, of the body movement data, a decision about whether or not there are any symptoms of an onset of a particular event related to the subject.

A sensor signal processing system according to another aspect of the present disclosure includes an acquisition unit and an acceleration calculation unit. The acquisition unit acquires body movement data about a subject's body movement from a measuring device. The measuring device outputs the body movement data. The acceleration calculation unit calculates, based on the body movement data, acceleration of the subject's body movement.

An event prediction method according to still another aspect of the present disclosure includes: acquiring body movement data about a subject's body movement from a measuring device that outputs the body movement data; and making, based on a subset, acquired during a past reference period, of the body movement data, a decision about whether or not there are any symptoms of an onset of a particular event related to the subject.

A non-transitory storage medium according to yet another aspect of the present disclosure stores a program designed to make a computer system execute the event prediction method described above.

DESCRIPTION OF EMBODIMENTS

First Embodiment (1) Overview

An overview of a sensor signal processing system 1 and event prediction system 10 according to a first exemplary embodiment will be described with reference to FIGS. 1 and 2. The event prediction system 10 includes the sensor signal processing system 1.

Figure 1:
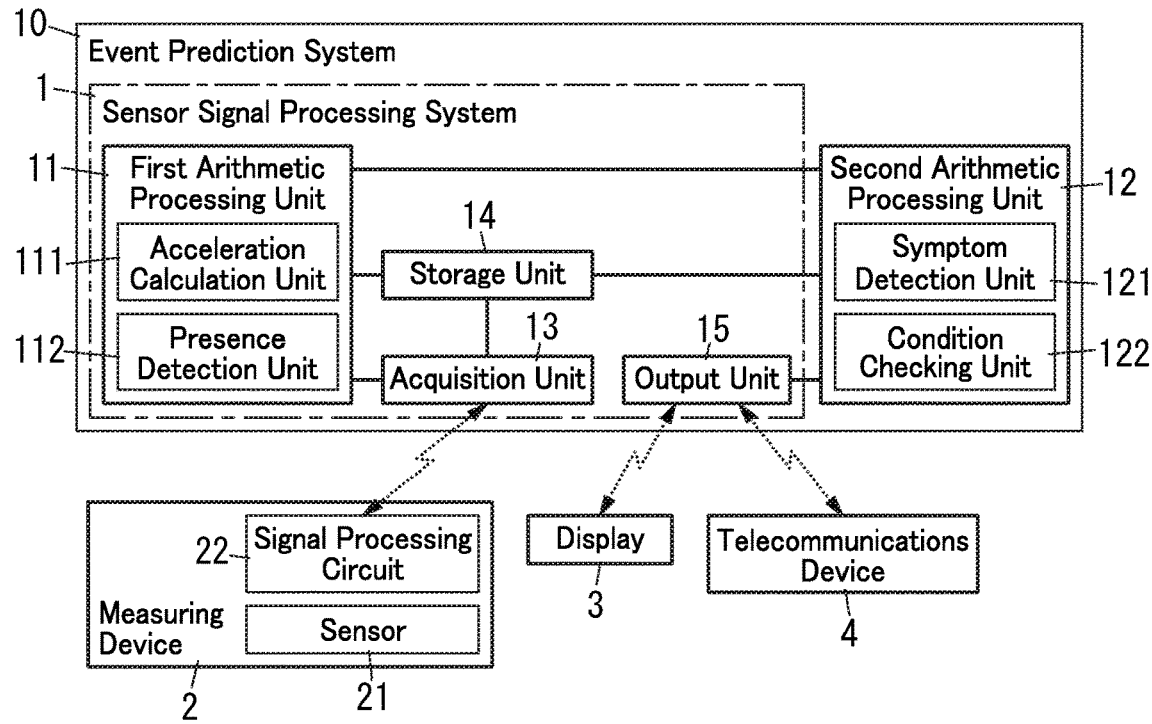
FIG. 1 is a block diagram illustrating a configuration for a sensor signal processing system and event prediction system according to a first embodiment of the present disclosure.
Figure 2:
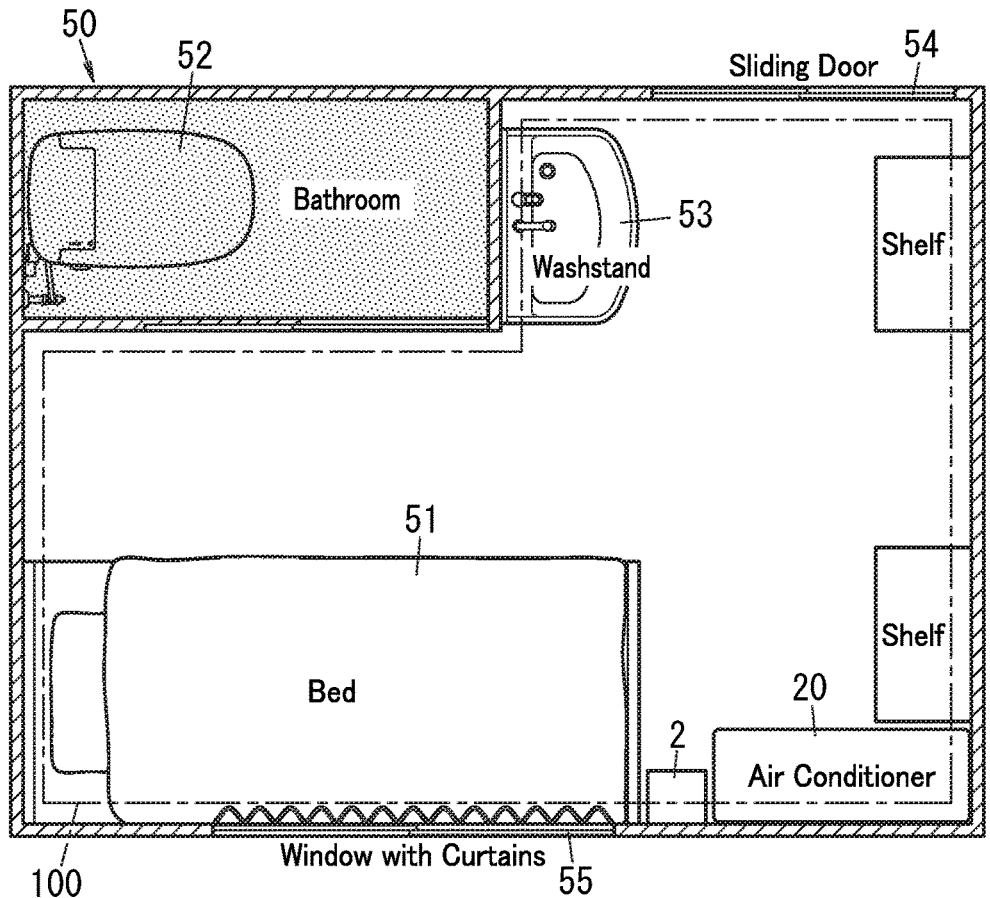
FIG. 2 depicts an exemplary facility to which the event prediction system is applicable.

The sensor signal processing system 1 is a system for performing signal processing on a sensor signal supplied from a measuring device 2 that monitors an object space 100 (see FIG. 2). The measuring device 2 includes a sensor 21 (see FIG. 1) that generates body movement data about the body movement of a subject (human) present in the object space 100 and outputs a sensor signal including the body movement data. The sensor signal processing system 1 includes an acceleration calculation unit 111 (see FIG. 1) for calculating, based on the body movement data, acceleration of the subject's body movement.

As used herein, the "object space" refers to a particular space in a facility such as a dwelling house with on-demand nursing care services for senior citizens, a nursing care facility, or a hospital. If the object space 100 is a space in a private room of a dwelling house with on-demand nursing care services for senior citizens or a nursing care facility, then the "subject" is the resident of the private room (i.e., a person to be taken care of). On the other hand, if the object space 100 is a space in a room of a hospital, then the "subject" is a patient hospitalized in the room of the hospital. Also, as used herein, the "body movement" refers to not only the body movement of a person sleeping or lying in a bed (such as rolling over) but also any other body movement of a person who is standing, seated, or walking in general. Furthermore, the "acceleration" refers herein to the ratio of a variation in the velocity of at least a part of the subject's body in motion (i.e., the movement velocity of that part) with respect to time. For example, if the subject is walking, he or she is moving his or her entire body. Thus, in that case, the "acceleration" is represented by the ratio of a variation in the velocity of the entire body movement with respect to time. On the other hand, if the subject lying in a bed has moved a part of his or her body, then the "acceleration" is represented by the ratio of a variation in the velocity of movement of that body part with respect to time.

That is to say, the sensor signal processing system 1 is allowed to quantitatively analyze, based on the body movement data acquired from the measuring device 2, the subject's movement as acceleration. The acceleration of the subject's body movement may be used to recognize the subject's condition such as the subject's behavior and his or her fitness level and to identify the subject.

The event prediction system 10 according to this embodiment is a system for making, based on the result of processing by the sensor signal processing system 1, a decision about any symptoms of the onset of a particular event related to the subject. As used herein, the "particular event" refers to a particular one selected from the group consisting of various events that could occur to the subject. Examples of such "particular events" include the onset of an illness requiring an end-of-life care, tumbling during walking, the onset of an illness or injury requiring hospitalization, death, a sharp decline in cognitive function (marking the onset of a cognitive disorder), and roaming. The "particular event" may also refer herein to any of the subject's individual actions in his or her daily life such as getting out of bed, excretion, and going to bed.

That is to say, the event prediction system 10 makes, based on the body movement data acquired from the measuring device 2, a decision about any symptoms of the onset of any of these particular events, i.e., a "sign" that appears before the particular event occurs. In other words, this event prediction system 10 is able to make a decision about a particular event that should occur very soon, instead of recognizing the subject's current condition. Thus, the event prediction system 10 according to this embodiment is able to make a decision about event symptoms of the onset of a particular event related to the subject, which is one of advantages of this event prediction system.

(2) Details

A sensor signal processing system 1 and event prediction system 10 according to a first exemplary embodiment will be described in detail with reference to the accompanying drawings. An exemplary embodiment will be described as being applied to a situation where the object space 100 is set in a private room 50 of a dwelling house with on-demand nursing care services for senior citizens as shown in FIG. 2. That is to say, in this specific example, the "subject" is a resident of the private room.

(2.1) Configuration

The event prediction system 10 includes the sensor signal processing system 1 as described above. In this embodiment, the event prediction system 10 further includes a second arithmetic processing unit 12 as shown in FIG. 1. The sensor signal processing system 1 and the event prediction system 10 including the sensor signal processing system 1 may be implemented as a computer system installed in a caretaker's room, for example, of the facility in which the object space 100 is set (e.g., a dwelling house with on-demand nursing care services for senior citizens).

The sensor signal processing system 1 receives a sensor signal from the measuring device 2 that monitors the object space 100. As described above, the measuring device 2 includes the sensor 21 for generating body movement data about the body movement of the subject (person) present in the object space 100 and outputs a sensor signal, including the body movement data, to the sensor signal processing system 1.

Note that in this embodiment, the measuring device 2 is not a constituent element of the sensor signal processing system 1 or the event prediction system 10. Thus, the sensor signal processing system 1 and the event prediction system 10 may be used in combination with any of various types of measuring devices 2. However, this is only an example and should not be construed as limiting. Alternatively, the sensor signal processing system 1 and the event prediction system 10 may each include the measuring device 2 as their constituent element.

The measuring device 2 includes a sensor 21 and a signal processing circuit 22. The sensor 21 is a noncontact sensor for detecting the subject's body movement without making physical contact with the subject. In short, the measuring device 2 generates body movement data about the subject's body movement by a noncontact method. This allows the measuring device 2 to generate the body movement data without interfering with the subject's movement. The measuring device 2 may be a radio wave Doppler sensor, for example.

The sensor 21 is a transducer with the ability to transform an electrical signal into a radio wave, and vice versa, and may be implemented as a radio wave sensor for transmitting and receiving radio waves in a micrometer band. The sensor 21 transmits radio waves to the object space 100 at regular time intervals (of one second, for example). The sensor 21 receives a wave (radio wave) reflected from any person (including the subject) present in the object space 100.

The signal processing circuit 22 performs signal processing on an output signal of the sensor 21 that has received the reflected wave (i.e., an electrical signal representing the reflected wave), thus generating body movement data representing the body movement of the subject present in the object space 100. Specifically, the signal processing circuit 22 compares the frequency of the radio wave received (i.e., the reflected wave) with the frequency of the radio wave transmitted, thus obtaining the movement velocity of the subject's body by utilizing the Doppler effect and generating body movement data. In this case, the movement velocity, obtained by the signal processing circuit 22, of the subject's body has the positive or negative sign, thereby providing information about the "direction of the body movement" indicating whether the body is moving toward, or away from, the sensor 21. That is to say, the body movement data generated by the signal processing circuit 22 may be handled as a vector value with a "direction" component. This allows the signal processing circuit 22 to decide whether the body is moving toward, or away from, the sensor 21, and thereby allows the signal processing circuit 22 to sense the subject getting out of bed. Furthermore, the acceleration obtained based on the body movement data may also be a vector value including a "direction" component.

In addition, in this embodiment, the signal processing circuit 22 also has the capability of generating measurement data indicating the subject's cardiac rate and respiratory condition by extracting a particular frequency component from the body movement data. Specifically, the signal processing circuit 22 generates measurement data indicating the cardiac rate (hereinafter referred to as "cardiac rate measurement data") by having the body movement data filtered by a cardiac rate filter and extracting a frequency component of the body movement caused by the cardiac rate. In addition, the signal processing circuit 22 also generates measurement data indicating the respiratory condition (hereinafter referred to as "respiratory measurement data") by having the body movement data filtered by a respiration filter and extracting a frequency component of the body movement caused by the respiration. In this case, the interval at which the signal processing circuit 22 generates the cardiac rate measurement data and the respiratory measurement data is longer than the interval at which the signal processing circuit 22 generates the body movement data. For example, the signal processing circuit 22 may generate the body movement data every second, and generate the cardiac rate measurement data and the respiratory measurement data every five seconds.

Furthermore, the signal processing circuit 22 outputs a sensor signal, including the body movement data, the cardiac rate measurement data, and the respiratory measurement data, to the sensor signal processing system 1. In this embodiment, the signal processing circuit 22 is configured to communicate with the sensor signal processing system 1 wirelessly in compliance with a wireless communications standard such as Bluetooth®. However, this is only an example and should not be construed as limiting. The measuring device 2 and the sensor signal processing system 1 do not have to be configured to communicate directly with each other but may also be configured to communicate with each other via a relay transmitter, for example.

The measuring device 2 is installed in the private room 50 in which the object space 100 is set as shown in FIG. 2. In the example depicted in FIG. 2, the private room 50 is provided with equipment including a bed 51, a bathroom with a toilet 52, a washstand 53, a sliding door 54 at the entrance, and a window 55. Note that these pieces of equipment including the bed 51, the toilet 52, the washstand 53, the sliding door 54, and the window 55 do not have to be provided for, but may be omitted as appropriate from, the private room 50. On a wall of the private room 50, installed is an air conditioner 20 for conditioning the air in the private room 50. In this embodiment, the measuring device 2 is arranged beside the air conditioner 20, for example.

In this example, the measuring device 2 is oriented to monitor the object space 100 including at least the surface of the bed 51. In this embodiment, the object space 100 is almost all space inside the private room 50 but the bathroom with the toilet 52. However, this is only an example and should not be construed as limiting. Alternatively, the object space 100 may also be the entire space inside the private room 50 or may be changed as appropriate.

The sensor signal processing system 1 includes a first arithmetic processing unit 11, an acquisition unit 13, a storage unit 14, and an output unit 15 as shown in FIG. 1.

The acquisition unit 13 acquires body movement data about the subject's body movement. That is to say, the acquisition unit 13 has the capability of communicating with (the signal processing circuit 22 of) the measuring device 2. In this embodiment, the acquisition unit 13 is configured to communicate with the measuring device 2 wirelessly in compliance with a wireless communications standard such as Bluetooth®. The acquisition unit 13 acquires at least the body movement data from the measuring device 2 by establishing communication with the measuring device 2 either periodically or non-periodically. Specifically, the acquisition unit 13 acquires the body movement data, along with the cardiac rate measurement data and the respiratory measurement data, by receiving the sensor signal from the measuring device 2. On receiving the data (including the body movement data, the cardiac rate measurement data, and the respiratory measurement data) from the measuring device 2, the acquisition unit 13 outputs the data acquired to the first arithmetic processing unit 11.

The first arithmetic processing unit 11 has at least the functions of an acceleration calculation unit 111 and a presence detection unit 112. The first arithmetic processing unit 11 may be implemented, for example, as a computer system including a processor and a memory. In other words, the computer system performs the functions of the acceleration calculation unit 111 and the presence detection unit 112 by making the processor of the first arithmetic processing unit 11 execute a program stored in the memory. The program may be stored in advance in either the memory of the first arithmetic processing unit 11 or the storage unit 14 or may also be downloaded via a telecommunications line such as the Internet or distributed after having been stored on a non-transitory storage medium such as a memory card.

The acceleration calculation unit 111 calculates, based on the body movement data, the acceleration of the subject's body movement. That is to say, if there is any movement in at least part of the subject's body, then the acceleration calculation unit 111 calculates, as the acceleration, the ratio of a variation in the velocity of movement of the at least part of the subject's body (movement velocity) with respect to time. In this embodiment, the acceleration calculation unit 111 calculates, based on the body movement data acquired by the acquisition unit 13 from the measuring device 2, the acceleration by a predetermined algorithm to perform acceleration calculation processing of generating data representing the acceleration (hereinafter referred to as "acceleration data"). The acceleration calculation processing by the acceleration calculation unit 111 will be described in detail later in the "(2.2.2) Acceleration calculation processing" section.

The presence detection unit 112 makes, based on the body movement data, a decision about whether the subject is present in, or absent from, the object space 100. The presence detection unit 112 performs presence detection processing of generating, based on the body movement data acquired by the acquisition unit 13 from the measuring device 2 and by a predetermined algorithm, data indicating whether the subject is present in, or absent from, the object space 100 (hereinafter referred to as "presence/absence data").

In this embodiment, the presence detection unit 112 performs time series analysis processing of obtaining an analysis model for a times series analysis in which the body movement data acquired at a predetermined timing is represented by multiple items, acquired before the predetermined timing, of body movement data. The acquisition unit 13 acquires measurement data from the measuring device 2 every second, for example. For instance, the time series analysis processing may be performed to obtain an analysis model for a time series analysis in which the body movement data acquired at a predetermined timing is represented by multiple items (e.g., 30 items), acquired before the predetermined timing, of body movement data. In this embodiment, the presence detection unit 112 obtains, by using an auto-regressive (AR) model, for example, an analysis model for an autocorrelation function in which the body movement data acquired at a predetermined timing is represented by 30 items of body movement data collected over the past 30 seconds. Note that the analysis model of the time series analysis performed by the presence detection unit 112 does not have to be the auto-regressive model but may also be any other analysis model such as an extended Kalman model. The analysis model may be changed as appropriate with the computational complexity and other factors taken into account.

The presence detection unit 112 decides, depending on a decision condition including a condition concerning a coefficient of the analysis model obtained by the time series analysis processing, whether the subject is present or absent at the predetermined timing. For example, the presence detection unit 112 may decide, depending on a decision condition that the coefficient of the analysis model obtained by the time series analysis processing should be greater than a predetermined threshold value or that the magnitude of the body movement data acquired should be greater than a predetermined decision value, whether the subject is present or absent at the predetermined timing. That is to say, the presence detection unit 112 determines, when finding a first-order coefficient of the auto-regressive model greater than the threshold value or finding the magnitude of the body movement data greater than a decision value, that the subject should be present in the object space 100 (i.e., he or she should be currently in the room). The presence detection unit 112 determines, when finding the first-order coefficient of the auto-regressive model equal to or less than the threshold value or finding the magnitude of the measurement data equal to or less than the decision value, that the subject should be absent from the object space 100 (i.e., he or she should be currently out of the room).

As can be seen, in the event prediction system 10 according to this embodiment, the presence detection unit 112 makes, depending on a decision condition concerning a coefficient of the analysis model obtained by the time series analysis processing, a decision about whether the subject is present or absent at a predetermined timing. This reduces the chances of the presence detection unit 112 being affected by a temporary variation in the measurement data, for example, thus improving the accuracy of the decision made by the presence detection unit 112.

Optionally, the presence detection unit 112 may decide, based on at least one of the cardiac rate measurement data, respiratory measurement data, and acceleration data, either instead of, or in addition to, the body movement data, whether the subject is present in, or absent from, the object space 100. That is to say, the presence detection unit 112 may perform, based on at least one of the body movement data, cardiac rate measurement data, respiratory measurement data, and acceleration data, the processing of deciding whether the subject is present in, or absent from, the object space 100. Each of the cardiac rate measurement data, respiratory measurement data, and acceleration data is based on the body movement data. Thus, it can be said that even when deciding, based on the acceleration data, whether the subject is present or not, the presence detection unit 112 is also making the decision (deciding whether the subject is present in, or absent from, the object space 100) based indirectly on the body movement data. In other words, the presence detection unit 112 may make, based on the body movement data either directly or indirectly, the decision about whether the subject is present in, or absent from, the object space 100.

In this case, when deciding, based on the acceleration data, whether or not the subject is present there, the presence detection unit 112 may also make the decision about the presence or absence of the subject by identifying the person present there. That is to say, the presence detection unit 112 may decide, based on the acceleration data, whether or not the person present there is the subject (i.e., the resident of the private room 50 in this example). This allows, if a person other than the subject (e.g., a facility staff member) is present in the object space 100, the presence detection unit 112 to determine that the subject should be absent from the object space 100 (i.e., somebody other than the subject should be present in the object space 100).

The second arithmetic processing unit 12 has at least the functions of a symptom detection unit 121 and a condition checking unit 122. Just like the first arithmetic processing unit 11, the second arithmetic processing unit 12 may also be implemented as a computer system including a processor and a memory. In other words, the computer system performs the functions of the symptom detection unit 121 and the condition checking unit 122 by making the processor of the second arithmetic processing unit 12 execute a program stored in the memory. The program may be stored in advance in either the memory of the second arithmetic processing unit 12 or the storage unit 14, or may also be downloaded via a telecommunications line such as the Internet or distributed after having been stored on a non-transitory storage medium such as a memory card. In this embodiment, the second arithmetic processing unit 12 is implemented as a different computer system from the first arithmetic processing unit 11.

The second arithmetic processing unit 12 receives the output data of the first arithmetic processing unit 11. In this embodiment, the output data of the first arithmetic processing unit 11 includes the body movement data, cardiac rate measurement data, and respiratory measurement data that the acquisition unit 13 has acquired from the measuring device 2. In addition, in this embodiment, the output data of the first arithmetic processing unit 11 further includes the acceleration data (i.e., data about the acceleration of the subject's body movement) obtained based on the body movement data by the acceleration calculation unit 111. The output data of the first arithmetic processing unit 11 further includes the presence/absence data (i.e., data indicating the decision made by the presence detection unit 112). Thus, the second arithmetic processing unit 12 receives not only the body movement data but also the cardiac rate measurement data, the respiratory measurement data, the acceleration data, and the presence/absence data. Each of the cardiac rate measurement data, respiratory measurement data, and acceleration data is obtained based on the body movement data, i.e., body movement data based data.

The symptom detection unit 121 makes, based on the body movement data, a decision about any symptoms of the onset of a particular event related to the subject. Specifically, the symptom detection unit 121 performs, based on the body movement data that the acquisition unit 13 has acquired from the measuring device 2 and by a predetermined algorithm, symptom detection processing of making a decision about any symptoms of the onset of a particular event such as the onset of an illness requiring an end-of-life care. In this case, the symptom detection unit 121 makes the decision about the symptoms based on a subset, acquired during a past reference period, of the body movement data. As used herein, the "reference period" refers to a period earlier than (i.e., prior to) a reference point in time when the symptom detection unit 121 makes the decision. In this embodiment, the reference period is a period with certain duration (of, e.g., 30 minutes, one hour, or one day) that terminates at the reference point in time. In other words, the symptom detection unit 121 performs the symptom detection processing based on the time series data of the body movement data, i.e., a set of the body movement data acquired by the acquisition unit 13 during the reference period that begins at a point in time earlier by the certain duration than the reference point in time and that ends at the reference point in time.

Optionally, the symptom detection unit 121, as well as the presence detection unit 112, may also make a decision about any symptoms of the onset of a particular event based on at least one of the cardiac rate measurement data, respiratory measurement data, and acceleration data, either instead of, or in addition to, the body movement data. That is to say, the symptom detection unit 121 may perform, based on at least one of the body movement data, cardiac rate measurement data, respiratory measurement data, and acceleration data included in the output data of the first arithmetic processing unit 11, the symptom detection processing of making a decision about any symptoms of the onset of a particular event. Each of the cardiac rate measurement data, respiratory measurement data, and acceleration data is based on the body movement data. In short, the symptom detection unit 121 may make a decision about any symptoms of the onset of a particular event based on the body movement data either directly or indirectly.

The decision made by the symptom detection unit 121 is output as symptom data to the output unit 15. In this embodiment, the symptom detection unit 121 only makes a decision about whether or not there are any symptoms of the onset of a particular event. In other words, the symptom detection unit 121 just decides, without distinguishing any one type of a particular event, for which a decision about the symptoms need to be made, from another, whether or not there are any symptoms of the onset of a particular event. Thus, the symptom data generated by the symptom detection unit 121 just indicates whether or not there are any symptoms of the onset of a particular event.

In addition, the symptom detection unit 121 also makes the decision about the symptoms in accordance with a variation, based on the body movement data, in the volume of the subject's physical activity. As used herein, the "volume of physical activity" is represented as the product of the intensity (or strength) of the physical activity and the duration of the physical activity. Also, as used herein, the "physical activity" refers to any type of activity conducted by the subject, and does not have to be an exercise practiced to maintain or improve the bodily strength but may also be every type of activity (or conduct) consuming a lot more energy than when the subject is at rest. The symptom detection processing to be carried out by the symptom detection unit 121 will be described in detail later in the "(2.2.3) Symptom detection processing" section.

The condition checking unit 122 checks, based on the body movement data, the subject's current condition, such as his or her fitness level, depth of sleep, and mental condition. That is to say, the condition checking unit 122 performs, based on the body movement data that the acquisition unit 13 has acquired from the measuring device 2 and by a predetermined algorithm, the condition checking processing of checking the subject's current condition indicating that he or she is in good or poor shape mentally and/or physically.

Optionally, the condition checking unit 122, as well as the symptom detection unit 121, may also check the subject's current condition based on at least one of the cardiac rate measurement data, respiratory measurement data, and acceleration data, either instead of, or in addition to, the body movement data. That is to say, the condition checking unit 122 may perform, based on at least one of the body movement data, cardiac rate measurement data, respiratory measurement data, and acceleration data included in the output data of the first arithmetic processing unit 11, the condition checking processing of checking the subject's current condition. In short, the condition checking unit 122 may make a decision about the subject's current condition based on the body movement data either directly or indirectly.

The decision made by the condition checking unit 122 is output as condition data to the output unit 15. In addition, the output data of the first arithmetic processing unit 11, namely, the body movement data, cardiac rate measurement data, respiratory measurement data, acceleration data, and presence/absence data, is also output from the second arithmetic processing unit 12 to the output unit 15.

The storage unit 14 may be implemented as, for example, an electrically programmable nonvolatile memory such as an electrically erasable programmable read-only memory (EEPROM) or a volatile memory such as a random access memory (RAM). The storage unit 14 stores the body movement data, cardiac rate measurement data, and respiratory measurement data that the acquisition unit 13 has acquired. In this embodiment, the storage unit 14 stores at least the body movement data collected over the reference period. The storage unit 14 also stores the results (including acceleration data and presence/absence data) of the arithmetic processing performed by the first arithmetic processing unit 11 and the results (including symptom data and condition data) of the arithmetic processing performed by the second arithmetic processing unit 12.

The output unit 15 outputs the decision made by the symptom detection unit 121. The output unit 15 also outputs the decisions made by the presence detection unit 112 and the condition checking unit 122. In this embodiment, the output unit 15 has the capability of communicating with some external devices such as a display 3 and telecommunications device 4. Examples of the telecommunications devices 4 include a smartphone, a tablet computer, and a personal computer. The output unit 15 outputs the data provided by the second arithmetic processing unit 12 to these devices.

That is to say, the presence/absence data generated by the presence detection unit 112, the symptom data generated by the symptom detection unit 121, and the condition data generated by the condition checking unit 122 are output from the output unit 15 to the display 3 and the telecommunications device 4. The output unit 15 may output the decision when the decision made by the presence detection unit 112, symptom detection unit 121, or condition checking unit 122 has changed. Alternatively, the output unit 15 may output the decision when requested by the telecommunications device 4 to do that, for example.

As a result, the decisions made by the presence detection unit 112, the symptom detection unit 121, and the condition checking unit 122 are presented to the caretaker on or via the display 3 and the telecommunications device 4. This allows the caretaker to check out the decisions made by the presence detection unit 112, the symptom detection unit 121, and the condition checking unit 122 on or via the display 3 and the telecommunications device 4. These decisions may be presented on or via the display 3 and the telecommunications device 4 by displaying image information there, emitting a voice message providing the information, printing out the information provided, writing the information on a non-transitory storage medium, or transmitting the information to another telecommunications device.

Optionally, the output unit 15 may also output the results of the arithmetic processing (namely, the acceleration data) performed by the acceleration calculation unit 111. In this embodiment, the output unit 15 outputs the decisions to those external devices including the display 3 and the telecommunications device 4 by communicating with those external devices. However, this is only an example and should not be construed as limiting. Alternatively, the output unit 15 may also output the decisions by itself by displaying image information there, emitting a voice message providing the information, printing out the information provided, writing the information on a non-transitory storage medium, or transmitting the information to another telecommunications device.

(2.2) Operation (2.2.1) Overall Operation

Next, the overall operation of a sensor signal processing system 1 and an event prediction system 10 including the sensor signal processing system 1 according to this embodiment will be described with reference to the flowchart of FIG. 3.

The acquisition unit 13 performs acquisition processing of acquiring body movement data from the measuring device 2 either periodically or non-periodically (in Step S1). In this embodiment, the acquisition unit 13 acquires the body movement data, cardiac rate measurement data, and respiratory measurement data from the measuring device 2 every second, for example. Then, the acquisition unit 13 outputs the data (namely, the body movement data, cardiac rate measurement data, and respiratory measurement data) acquired from the measuring device 2 to the first arithmetic processing unit 11. In this embodiment, the measuring device 2 is supposed to update the body movement data every second and also update the cardiac rate measurement data and the respiratory measurement data every five seconds. Thus, the cardiac rate measurement data and respiratory measurement data that the acquisition unit 13 has acquired from the measuring device 2 are updated every five seconds.

The first arithmetic processing unit 11 performs, on receiving the data (namely, the body movement data, cardiac rate measurement data, and respiratory measurement data) from the acquisition unit 13, preprocessing such as noise reduction and calculating the moving average on these data (in Step S2). The first arithmetic processing unit 11 stores the preprocessed data in the storage unit 14.

Then, the first arithmetic processing unit 11 makes the acceleration calculation unit 111 perform acceleration calculation processing based on the preprocessed body movement data, for example, thus obtaining acceleration data representing the acceleration (in Step S3). The acceleration calculation processing will be described in detail later in the "(2.2.2) Acceleration calculation processing" section.

Next, the first arithmetic processing unit 11 makes the presence detection unit 112 perform presence detection processing based on the preprocessed body movement data, for example, thus making, by time series analysis, a decision about whether the subject is present in, or absent from, the object space 100 (in Step S4).

If the result of the presence detection processing is that the subject should be present in the object space 100 (i.e., if the answer is YES in Step S5), then the second arithmetic processing unit 12 makes the symptom detection unit 121 perform symptom detection processing based on the preprocessed body movement data, for example, thus making a decision about any symptoms of the onset of a particular event (in Step S6). The symptom detection processing will be described in detail later in the "(2.2.3) Symptom detection processing" section.

Subsequently, the second arithmetic processing unit 12 makes the condition checking unit 122 perform condition checking processing based on the preprocessed body movement data, for example, thus making a decision about the subject's current condition (in Step S7).

Then, the output unit 15 performs output processing of outputting the decisions made by the presence detection unit 112, symptom detection unit 121, and condition checking unit 122 (in Step S8). Meanwhile, if the decision made by the presence detection processing is that the subject should be absent from the object space 100 (i.e., if the answer is NO in Step S5), then the symptom detection processing and the condition checking processing are skipped and the process proceeds to the output processing. In that case, the output unit 15 outputs only the decision made by the presence detection unit 112 in the output processing.

The sensor signal processing system 1 and the event prediction system 10 including the sensor signal processing system 1 may perform this series of processing steps S1-S8 repeatedly every second, for example.

Figure 3:
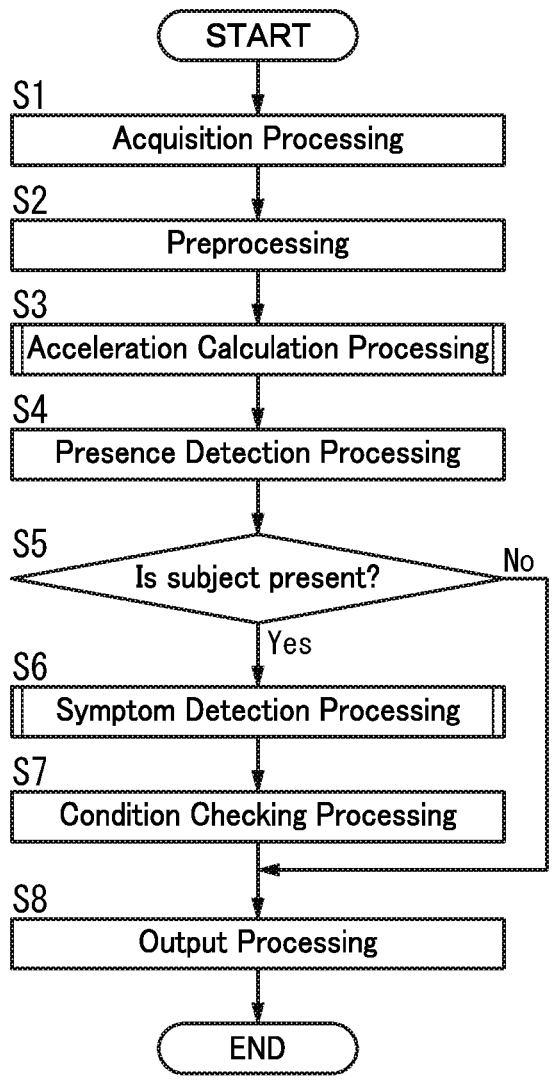
FIG. 3 is a flowchart illustrating how the event prediction system may operate.

Note that the order of the processing steps shown in FIG. 3 is only an example and may be changed as appropriate.

(2.2.2) Acceleration Calculation Processing

Next, it will be described how the acceleration calculation unit 111 performs the acceleration calculation processing (the processing step S3 shown in FIG. 3).

In performing the acceleration calculation processing, the acceleration calculation unit 111 calculates the acceleration by subjecting multiple items, arranged time sequentially, of body movement data to differential processing. Specifically, the acceleration calculation unit 111 calculates the acceleration of the subject's body movement during a predetermined period by performing differentiation on the multiple items, stored in the storage unit 14 and arranged time sequentially, of body movement data.

Specifically, the acceleration refers herein to the ratio of a variation in the velocity of at least a part of the subject's body in motion, if any, (i.e., the movement velocity of that part) with respect to time. On the other hand, the body movement data is data reflecting the velocity of the subject's movement. Thus, in the acceleration calculation processing, the acceleration calculation unit 111 calculates a differential value of the body movement data as the acceleration, thus generating acceleration data. Therefore, if the subject's movement velocity represented by the body movement data shows no variation with time (i.e., if the movement velocity is constant), then the acceleration obtained by the acceleration calculation processing becomes equal to zero. The more significant the variation with time in the subject's movement velocity reflected by the body movement data is, the greater the acceleration calculated by the acceleration calculation processing becomes.

Figure 4:
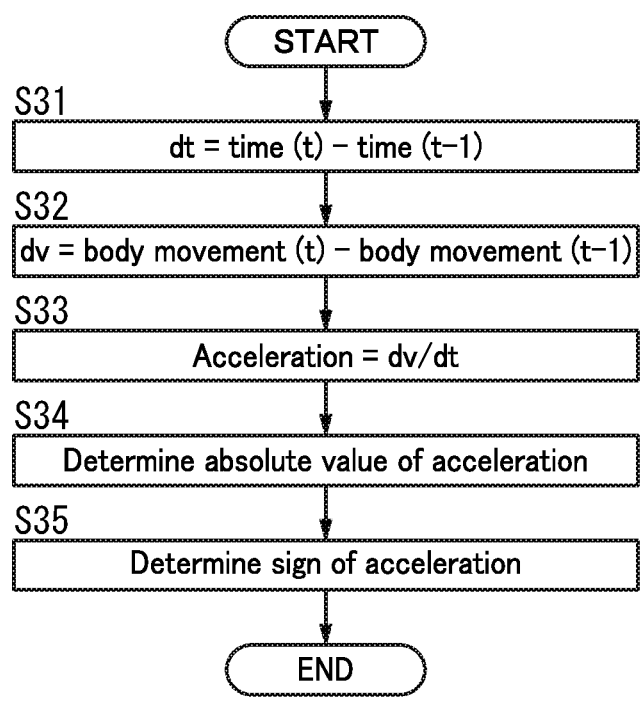
FIG. 4 is a flowchart illustrating a specific exemplary procedure of acceleration calculation processing to be performed by the event prediction system.

FIG. 4 is a flowchart showing a specific example of the acceleration calculation processing.

As shown in FIG. 4, when the acceleration calculation processing starts, the acceleration calculation unit 111 calculates a time difference dt between two adjacent ones, arranged time sequentially, of the multiple items of body movement data (in Step S31). In this example, take, as an example, an item of body movement data acquired at a predetermined timing t and another item of body movement data acquired at a timing t−1 preceding the predetermined timing t. In this case, the acceleration calculation unit 111 obtains, as the time difference dt, the difference between a time (t) corresponding to the predetermined timing t and a time (t−1) corresponding to the previous timing t−1.

Next, the acceleration calculation unit 111 calculates the variation dv in the value (magnitude) of the body movement data between the two adjacent items of the body movement data (in Step S32). In this case, the acceleration calculation unit 111 obtains, as the variation dv, the difference between the body movement (t) detected at the predetermined timing t and the body movement (t−1) detected at the previous timing t−1.

Subsequently, the acceleration calculation unit 111 obtains acceleration data by dividing the variation dv by the time difference dt (in Step S33). This allows the acceleration calculation unit 111 to determine the absolute value of the acceleration (in Step S34) and also determine the (positive or negative) sign of the acceleration (in Step S35). The absolute value of the acceleration corresponds to the magnitude of the subject's movement. The positive or negative sign of the acceleration indicates the direction of the subject's movement (i.e., whether the subject is moving toward, or away from, the sensor 21).

Note that the order of the processing steps shown in FIG. 4 is only an example and may be changed as appropriate.

In this example, the body movement data to be subjected to the differential processing may be either the body movement data yet to be preprocessed or the body movement data subjected to the preprocessing such as noise reduction or calculating the moving average. Performing the acceleration calculation processing based on the preprocessed body movement data reduces the harmful effect of noise.

(2.2.3) Symptom Detection Processing

Next, it will be described how the symptom detection unit 121 performs symptom detection processing (i.e., the processing step S6 shown in FIG. 3).

When performing the symptom detection processing, the symptom detection unit 121 makes a decision about any symptoms of the onset of a particular event based on a subset, acquired during a past reference period, of the body movement data. Specifically, the symptom detection unit 121 analyzes the multiple items, stored in the storage unit 14 and arranged time sequentially, of body movement data in terms of their data size, the magnitude of variation, the frequency of variation, and the time range of the variation, thus making a decision about any symptoms of the onset of a particular event based on the results of the analysis.

That is to say, before a particular event occurs, the body movement data of the subject tends to show a characteristic trend. The time series data of the body movement data is particularly likely to show such a characteristic trend. Thus, in performing the symptom detection processing, the symptom detection unit 121 analyzes the time series data of the body movement data in terms of their average (data size), the magnitude of variation, the frequency of variation, and the time range of the variation, thus making a decision about any symptoms of the onset of a particular event and generating symptom data. Therefore, when some characteristic trend, such as a significant continuous decrease in the average of the body movement data, is observed, for example, the result of the symptom detection processing will be that there should be some symptoms of the onset of an illness requiring an end-of-life care.

Figure 5:
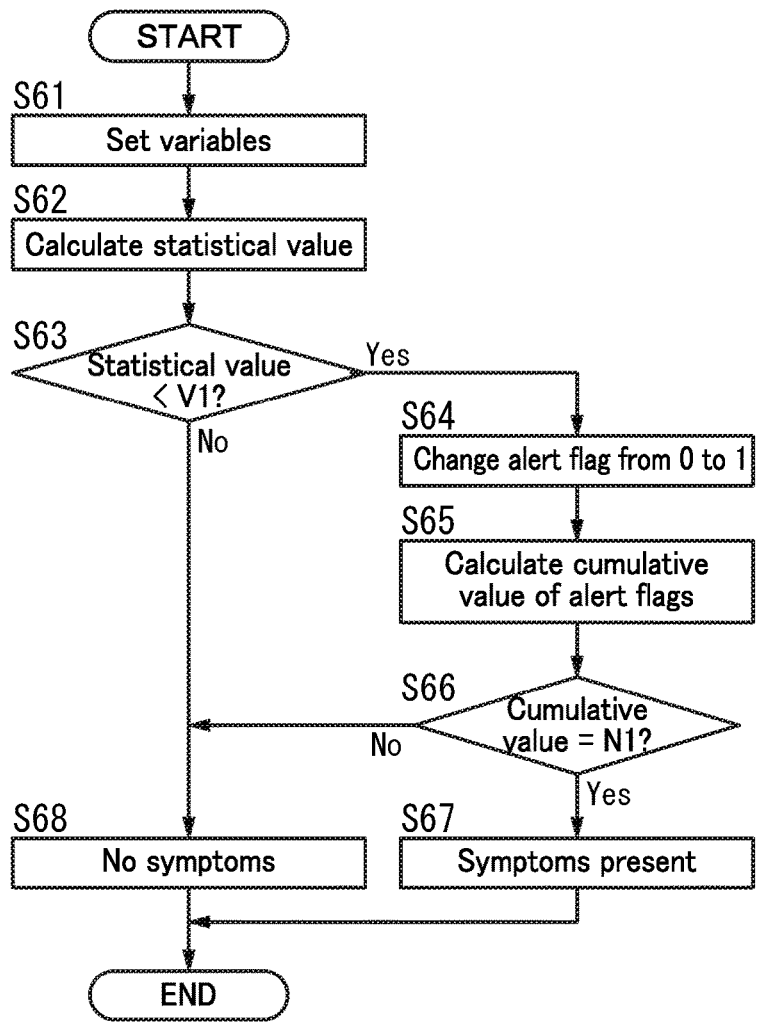
FIG. 5 is a flowchart illustrating a specific exemplary procedure of symptom detection processing to be performed by the event prediction system.

FIG. 5 is a flowchart showing a specific exemplary procedure of the symptom detection processing.

As shown in FIG. 5, when the symptom detection processing starts, first of all, the symptom detection unit 121 sets various types of variables (in Step S61). Examples of the variables to be set in this processing step include a threshold value V1 to be compared with a statistical value such as the body movement data, the starting date of the symptom detection processing, a data collection period, and a prescribed value N1 (to be described later).

Next, the symptom detection unit 121 calculates a statistical value such as the body movement data for the data collection period since the starting date (in Step S62). As used herein, the "statistical value" refers to a value obtained statistically based on time series data such as the body movement data (including the acceleration data) collected over the data collection period. Examples of the statistical value include the average (moving average), median, mode, minimum, and variance of the body movement data.

The symptom detection unit 121 compares the statistical value calculated with the threshold value V1 (in Step S63). If the statistical value is less than the threshold value V1 (i.e., if the answer is YES in Step S63), then the symptom detection unit 121 changes the value of an alert flag from zero to one (in Step S64). In addition, the symptom detection unit 121 also calculates the cumulative value of alert flags with a value of one during the data collection period (in Step S65).

Next, the symptom detection unit 121 compares the calculated cumulative value of the alert flags with a prescribed value N1 (in Step S66). When finding the cumulative value equal to the prescribed value N1 (i.e., if the answer is YES in Step S66), the symptom detection unit 121 determines that there should be some symptoms of the onset of a particular event (in Step S67). On the other hand, when finding the statistical value equal to or greater than the threshold value V1 (i.e., if the answer is NO in Step S63) or when finding the cumulative value less than the prescribed value N1 (i.e., if the answer is NO in Step S66), the symptom detection unit 121 determines that there should be no symptoms of the onset of a particular event (in Step S68).

Note that the order of the processing steps shown in FIG. 5 is only an example and may be changed as appropriate.

The flowchart of FIG. 5 shows the procedure of the symptom detection processing to be performed to make a decision about any symptoms of the onset of some long-term event (with a duration of a few days to several weeks or more, for example) such as the onset of an illness requiring hospitalization. However, this is only an example and should not be construed as limiting. Alternatively, the symptom detection processing may also be performed to make a decision about any symptoms of the onset of a much shorter-term event (with a duration of a few minutes to several hours or less) such as a lying person's getting out of bed. In making a decision about symptoms of the onset of such a short-term event (with a duration of a few minutes to several hours or less), the inequality sign in the processing step S63 of comparing the statistical value with the threshold value V1 is inverted from the one shown in FIG. 5. Furthermore, the duration of the particular event, for which a decision about its symptoms are to be made by the symptom detection processing, may be switched from the long-term one into the short-term one, or vice versa, by changing the length of the reference period to be set in the processing step S61, for example. When the length of the reference period is set at 60 days, for example, the symptom detection unit 121 may make a decision about any symptoms of the onset of a long-term particular event at a point of variation with an interval of 60 days. On the other hand, when the length of the reference period is set at 10 seconds, the symptom detection unit 121 may make a decision about any symptoms of the onset of a short-term particular event at a point of variation with an interval of 10 seconds.

Figure 6:
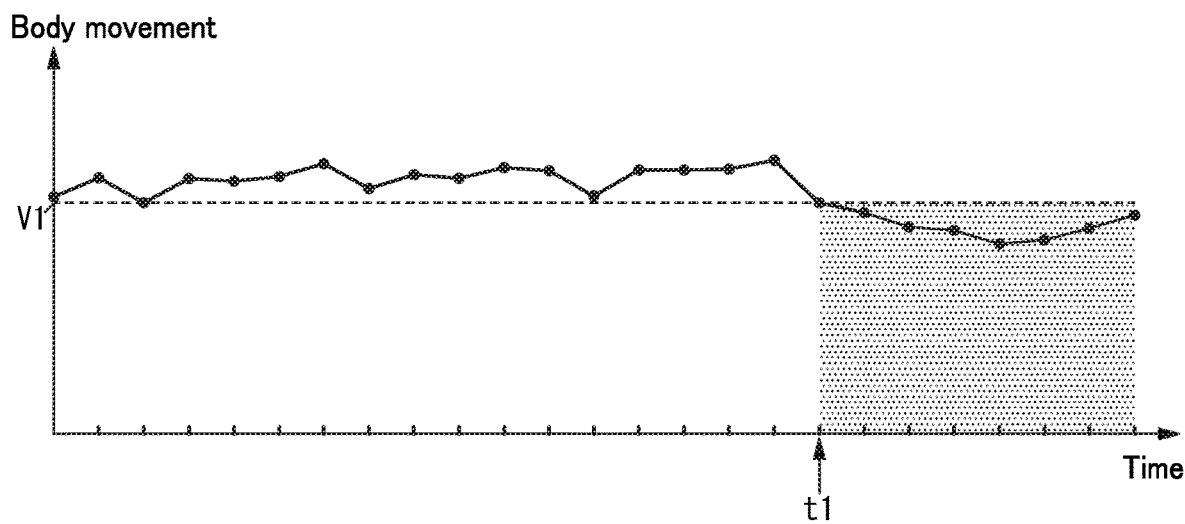
FIG. 6 is a graph showing exemplary body movement data to which the event prediction system is applicable.

Next, it will be described by way of example how to perform the symptom detection processing in the situation illustrated in FIG. 6. FIG. 6 is a graph showing a variation in body movement data. In FIG. 6, the abscissa indicates the time and the ordinate indicates the average (moving average) of the body movement data. Also, in FIG. 6, one step on the axis of abscissas corresponds to five days.

In the example illustrated in FIG. 6, before a time t1, the average of the body movement data remains equal to or greater than the threshold value V1. On the other hand, from the time t1 and on, the average of the body movement data becomes less than the threshold value V1. In other words, the average of the body movement data becoming less than the threshold value V1 at the time t1 manifests a different trend from the one before the time t1. The subject of this example had an attack of an illness requiring hospitalization a few days after the time t1. That is to say, the symptoms of the onset of a particular event, which is the onset of an illness requiring hospitalization in this example, manifested themselves at the time t1 as a characteristic trend of the subject's body movement data.

In particular, according to this embodiment, the symptom detection unit 121 is able to detect the symptoms in accordance with a variation, based on the body movement data, in the volume of the subject's physical activity, as described above. In this case, the subject's physical activity is calculated by the Newton's force equation: $F=ma$, where F indicates the force that is the product of acceleration and mass. When the subject is conducting a physical activity using his or her whole body, the subject's weight corresponds to the mass. Supposing an increase or decrease in the subject's weight is negligible, the acceleration will correspond to the muscular strength that the subject exerted to conduct the physical activity. Thus, the acceleration obtained by the acceleration calculation unit 111 corresponds to the strength of the physical activity and the volume of the physical activity during a certain period is represented as the cumulative value of the acceleration during the certain period. Thus, in this embodiment, when performing the symptom detection processing, the symptom detection unit 121 makes a decision about any symptoms of the onset of a particular event based on the acceleration data obtained by the acceleration calculation processing.

Decision conditions for use in the symptom detection processing include the following four conditions, which will be hereinafter referred to as first, second, third, and fourth conditions, respectively. The first condition is that the volume of the physical activity should remain equal to or less than a first threshold value for a first amount of time (which ranges from a few days to several weeks). The second condition is that the magnitude of decrease in the physical activity during a second period of time (which ranges from a few ten minutes to several hours) be equal to or greater than a second threshold value. The third condition is that the volume of the physical activity be equal to or less than a third threshold value (which is less than the first threshold value). The fourth condition is that the difference between the average volume of the physical activity while the subject is at rest (e.g., sleeping) and that of the physical activity while he or she is not at rest be equal to or less than a fourth threshold value. Conditional formulae and parameters (including threshold values) for meeting these decision conditions may be stored, for example, in the storage unit 14.

In another example, the symptom detection processing may also be performed to make a decision about any symptoms of the onset of a particular event by using body movement data as a vector value. In that case, the symptom detection unit 121 analyzes not only a scalar quantity such as the average of the body movement data but also the acceleration data as a vector value including a "direction" component. This allows the symptom detection unit 121 to determine, when sensing the subject move out of the private room 50, that there should be some symptoms of the onset of a particular event such as roaming or a sharp decline in cognitive function.

Optionally, the decision conditions (including the magnitude of the threshold value and the length of the period) for use in the symptom detection processing may be set on an individual basis for each subject. Thus, in a dwelling house with on-demand nursing care services for senior citizens and with multiple private rooms 50, for example, the decision conditions for use in the symptom detection processing may be set on an individual basis for each private room 50.

(3) Variations

The first embodiment described above is only one of various embodiments of the present disclosure, and may be readily modified, changed, replaced, or combined with any other embodiments, depending on a design choice or any other factor, without departing from a true spirit and scope of the present disclosure. Also, the same function as that of the sensor signal processing system 1 according to the first embodiment may be implemented as a sensor signal processing method, a (computer) program of processing a sensor signal, or a non-transitory storage medium that stores the program thereon. A sensor signal processing method according to an aspect includes: acquiring body movement data from a measuring device 2 that outputs body movement data representing a subjects body movement (in Step S1 shown in FIG. 3); and obtaining, based on the body movement data, acceleration of the subjects body movement (in Step S3 shown in FIG. 3). A program according to another aspect is designed to make a computer system execute the sensor signal processing method. Furthermore, the same function as that of the event prediction system 10 may be implemented as an event prediction method, a (computer) program of predicting an event, or a non-transitory storage medium that stores the program thereon. An event prediction method according to another aspect includes: acquiring body movement data about a subject's body movement (in Step S1 shown in FIG. 3); and making, based on the body movement data, a decision about whether or not there are any symptoms of the onset of a particular event related to the subject (in Step S6 shown in FIG. 3). A program according to another aspect is designed to make a computer system execute the event prediction method.

Next, variations of the first embodiment will be enumerated one after another. Optionally, any of the variations to be described below may be adopted in combination as appropriate.

The sensor signal processing system 1, event prediction system 10, and the agent that carries out the sensor signal processing method or event prediction method according to the present disclosure may each include a computer system. In that case, the computer system may include, as principal hardware components, a processor and a memory. The function of the sensor signal processing system 1, event prediction system 10, and the agent that carries out the sensor signal processing method or event prediction method according to the present disclosure may be performed by making the processor execute the program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be made up of a single or a plurality of electronic circuits including a semiconductor integrated circuit (IC) or a largescale integrated circuit (LSI). Those electronic circuits may be integrated together on a single chip or distributed on multiple chips without limitation. Those multiple chips may be integrated together in a single device or distributed in multiple devices without limitation.

Also, the plurality of functions of the sensor signal processing system 1 does not have to be aggregated together in a single housing. Rather, the respective constituent elements of the sensor signal processing system 1 may be distributed in multiple housings. Optionally, at least some of the functions of the sensor signal processing system 1 may be performed by a server and cloud computing system, for example. Likewise, the plurality of functions of the event prediction system 10 does not have to be aggregated together in a single housing. Rather, the respective constituent elements of the event prediction system 10 may be distributed in multiple housings. Optionally, at least some of the functions of the event prediction system 10 may be performed by a server and cloud computing system, for example. Conversely, the functions distributed in multiple devices in the first embodiment, such as the measuring device 2 and the sensor signal processing system 1, may be aggregated together in a single housing.

Furthermore, the facility in which the object space is set does not have to be a dwelling house with on-demand nursing care services for senior citizens, a nursing care facility, a hospital, or any other facility with a resident caregiver but may also be a child care facility such as a nursery. In the latter case, the subject is an infant or a child to be taken care of. Alternatively, the facility in which the object space is set may also be a general dwelling house (such as a single-family dwelling house or a multi-family dwelling house). In that case, the subject is a resident of the dwelling house. In a situation where the subject lives alone in the facility where the object space is set, the decision made by the event prediction system 10 will be transmitted as a notification to the subject's family member living separately from the subject, a care manager or social worker in the district where the subject lives, or any other appropriate person.

Moreover, the measuring device 2 only needs to be configured to output at least the body movement data to the sensor signal processing system 1. That is to say, the sensor signal processing system 1 does not have to output other types of data (namely, the cardiac rate measurement data and the respiratory measurement data).

Besides, the measuring device 2 does not have to be a radio wave Doppler sensor but may also be an ultrasonic Doppler sensor that transmits an ultrasonic wave as well. Also, the measuring device 2 only needs to generate body movement data about the body movement of the subject present in the object space 100. Thus, the measuring device 2 does not have to be a Doppler sensor but may also be a radio wave sensor that employs a frequency modulation continuous wave radar method or a sensor that uses a time of flight (TOF) method or an image sensor. Furthermore, the measuring device 2 does not have to be a noncontact sensor that generates body movement data about the subject's body movement by a noncontact method but may also be a contact-type sensor such as a wearable terminal to be used in contact with the subject's body.

Furthermore, the symptom detection unit 121 only needs to make a decision about any symptoms of the onset of a particular event based on the body movement data, to say the least. That is to say, the symptom detection unit 121 configured to make a decision about any symptoms of the onset of a particular event based on the acceleration data is not an essential constituent element for the event prediction system 10. Rather the acceleration calculation unit 111 may be omitted when the symptom detection unit 121 does not use the acceleration data.

Furthermore, in the event prediction system 10, the sensor signal processing system 1 thereof does not have to include the acquisition unit 13, the storage unit 14, and the output unit 15. Alternatively, the event prediction system 10 may include the acquisition unit 13, the storage unit 14, and the output unit 15 separately from the sensor signal processing system 1. The storage unit 14 and the output unit 15 are not essential constituent elements of the event prediction system 10, either. Thus, at least one of the storage unit 14 or the output unit 15 may be omitted as appropriate.

Furthermore, the acceleration data generated by the acceleration calculation unit 111 does not have to be used by the symptom detection unit 121, the condition checking unit 122, and other units. Alternatively, the acceleration data may be used only to have a decision made by the presence detection unit 112, for example. Still alternatively, the result of calculation obtained by the acceleration calculation unit 111 may just be output to the output unit 15. In that case, the symptom detection unit 121 and the condition checking unit 122 are not essential constituent elements for the event prediction system 10, and therefore, at least one of the symptom detection unit 121 or the condition checking unit 122 may be omitted.

Furthermore, the method of communications between the measuring device 2 and the sensor signal processing system 1 does not have to be a wireless communication but may also be a wired communication (including a power line carrier communication).

Optionally, the first arithmetic processing unit 11 and the second arithmetic processing unit 12 may be implemented as a single computer system. Conversely, the first arithmetic processing unit 11 and the second arithmetic processing unit 12 may also be implemented as three or more computer systems.

Optionally, a technique such as machine learning is applicable to some processing (such as acceleration calculation processing and symptom detection processing) to be performed by the sensor signal processing system 1 and the event prediction system 10. For example, the technique such as machine learning is suitably used under a decision condition specifying on what criteria a decision about the symptoms need to be made based on a subset, acquired during a past reference period, of the body movement data.

For example, the threshold value V1 may be determined by not only the basal metabolic rate (BMR) that can be estimated by the age, height, weight, and other personal data of the subject but also machine learned data about, for example, the respiratory rate and cardiac rate measured as well. Furthermore, the threshold value V1 does not have to be a constant value but may have a gradient with respect to the time axis.

Optionally, the machine learning technique may also be used to set a time range for calculating the prescribed value N1 or the statistical value based on the age, height, weight, dietary intake, or any other parameter.

Furthermore, in the foregoing description of the first embodiment, if one of two values being compared with each other is "equal to or greater than" the other, this phrase may herein cover both a situation where these two values are equal to each other and a situation where one of the two values is greater than the other. However, this should not be construed as limiting. Alternatively, the phrase "equal to or greater than" may also be a synonym of the phrase "greater than" that covers only a situation where one of the two values is over the other. That is to say, it is arbitrarily changeable, depending on selection of the threshold value or any preset value, whether or not the phrase "equal to or greater than" covers the situation where the two values are equal to each other. Therefore, from a technical point of view, there is no difference between the phrase "equal to or greater than" and the phrase "greater than." Similarly, the phrase "less than" may be a synonym of the phrase "equal to or less than" as well.

Second Embodiment

In an event prediction system 10 according to a second exemplary embodiment, the symptom detection unit 121 performs its symptom detection processing in a different way from its counterpart of the event prediction system 10 according to the first embodiment. In the following description, any constituent member of the second embodiment having the same function as its counterpart of the first embodiment described above will be designated by the same reference numeral as that counterpart's, and a detailed description thereof will be omitted herein.

In this embodiment, the symptom detection unit 121 distinguishes one type of particular event, for which a decision about the symptoms need to be made, from another. In other words, the symptom detection unit 121 not only decides whether or not there are any symptoms of the onset of a particular event but also determines what type of particular event is going to happen. That is to say, on determining that there should be some symptoms of the onset of a particular event, the symptom detection unit 121 determines what type of particular event those symptoms should precede, among various types of events that could occur to the subject.

Examples of various types of particular events include the onset of an illness requiring an end-of-life care, tumbling during walking, the onset of an illness or injury requiring hospitalization, death, a sharp decline in cognitive function, roaming, getting out of bed, excretion, and going to bed. Nevertheless, particular events do not have to be classified by specific type such as the onset of an illness requiring an end-of-life care or tumbling during walking, but may also be classified more broadly by duration. That is to say, particular events may also be classified into long-term events with a duration of a few days to several weeks or more and short-term events with a duration of a few minutes to several hours or less. Therefore, the symptom data generated by the symptom detection unit 121 indicates whether or not there are any symptoms of the onset of a particular event, and also indicates, if there are any such symptoms, what type of particular event those symptoms should precede.

Specifically, the symptom detection unit 121 makes a decision about whether or not there are any symptoms of the onset of a particular event, while distinguishing one type of particular event from another based on decision conditions associated with respective types of particular events. Those decision conditions may be stored in the storage unit 14, for example. In this case, in the symptom detection processing, a score may be calculated depending on whether one decision condition is satisfied or not. If it is presumed that there should be multiple particular events, each of which satisfies a plurality of decision conditions, then one, satisfying a decision condition at the highest score, of those particular events may be selected.

In the example described above, the symptom detection unit 121 determines, after having determined that there should be some symptoms of the onset of a particular event, what type of particular event those symptoms should precede. However, this is only an example and should not be construed as limiting. Alternatively, the symptom detection unit 121 may also specify the type of a particular event of interest first, and then make a decision about whether or not there are any symptoms of the onset of that type of particular event. This allows the symptom detection unit 121 to narrow down types of particular events, for which a decision about the symptoms need to be made, to a specified type of particular event. For example, the type of particular event, for which a decision about the symptoms need to be made, is specified as the onset of an illness requiring an end-of-life care, then the symptom detection unit 121 does not make a decision about whether or not there are any symptoms of the onset of any other particular event such as a sharp decline in cognitive function.

Optionally, the decision conditions for use in the symptom detection processing may also include conditions concerning external information to be entered into the event prediction system 10 from outside of the event prediction system 10. Examples of pieces of such external information include the subject's nursing care level, anamnesis, and nursing care record. This allows the symptom detection unit 121 to improve the accuracy of decision made through the symptom detection processing by reference to those pieces of information including the nursing care level, anamnesis, and nursing care record.

Furthermore, the output unit 15 may also change, according to such external information, the order and mode in which the decisions made by the symptom detection unit 121 are presented to the caretaker, for example. Specifically, if decisions are made almost simultaneously with respect to a plurality of subjects that there be some symptoms of the onset of a particular event, then the presentations of the decisions may be prioritized in accordance with pieces of external information about those subjects such that the decision may be presented to the subject of a top priority earlier than anybody else.

Moreover, the symptom detection unit 121 may change, in accordance with past body movement data or decision, the decision condition for use in the symptom decision processing from one subject to another. This allows the symptom detection unit 121 to make a decision about any symptoms of the onset of a particular event according to life rhythms and physical conditions that vary from one subject to another, thus improving the accuracy of the decision made by the symptom detection processing.

Besides, the event prediction system 10 may also use, based on the decisions of the symptom detection processing, events involved with those decisions of the symptom detection processing as feedback information. Examples of those events involved include the details of the nursing care carried out by the caregiver (i.e., a person who takes care of the subject), and a variation in the physical condition of the subject who has been given the nursing care. This allows the event prediction system 10 to utilize the feedback information to propose what type of care should be given to him or her, considering the decision, and check the validity of the decision made through the symptom detection processing.

If necessary, the event prediction system (10) may output the result of the symptom detection processing to an external nursing care service system, for example. Furthermore, the output unit (15) may change, depending on the result of the symptom detection processing, the destination to which the result of the symptom detection processing is to be output. This allows the output unit (15) to change, depending on what type of particular event the decision result indicates those symptoms should precede, the person, to whom the result of the symptom detection processing should be presented, from one of a doctor, a nurse, or a caregiver to another.

Optionally, the configuration of the event prediction system (10) according to the second embodiment may be appropriately combined with any of various configurations described for the first embodiment (including variations thereof).

(Resume)

As can be seen from the foregoing description, an event prediction system (10) according to a first aspect includes an acquisition unit (13) and a symptom detection unit (121). The acquisition unit (13) acquires body movement data about a subject's body movement. The symptom detection unit (121) makes, based on the body movement data, a decision about whether or not there are any symptoms of the onset of a particular event related to the subject.

This aspect allows for detecting, based on body movement data, symptoms of the onset of a particular event that could occur to the subject, i.e., a "sign" that appears before the particular event occurs. Thus, this event prediction system (10) allows the user to detect event symptoms of the particular event related to the subject, which is one of advantages of this event prediction system.

In an event prediction system (10) according to a second aspect, which may be implemented in conjunction with the first aspect, the symptom detection unit (121) makes the decision about the symptoms based on a subset, acquired during a past reference period, of the body movement data.

This aspect allows symptoms to be detected relatively by reference to a subset, acquired during a past reference period, of the body movement data. This curbs a decline in symptom detection accuracy even if the body movement data varies from one subject to another.

In an event prediction system (10) according to a third aspect, which may be implemented in conjunction with the first or second aspect, the symptom detection unit (121) makes the decision about the symptoms in accordance with a variation, obtained based on the body movement data, in volume of the subject's physical activity.

This aspect improves the symptom detection accuracy. Specifically, symptoms of the onset of a particular event often appear as a variation in the volume of the subject's physical activity. Thus, having the symptom detection unit (121) detect a symptom based on such a variation in the volume of physical activity improves the detection accuracy.

An event prediction system (10) according to a fourth aspect, which may be implemented in conjunction with any one of the first to third aspects, further includes a presence detection unit (112). The presence detection unit (112) is configured to make, based on the body movement data, a decision about whether the subject is present in, or absent from, an object space (100).

This aspect allows the body movement data to be used for both detecting symptoms of the onset of a particular event and detecting presence or absence of the subject in a given object space (100).

An event prediction system (10) according to a fifth aspect, which may be implemented in conjunction with any one of the first to fourth aspects, further includes an output unit (15). The output unit (15) is configured to output the decision made by the symptom detection unit (121).

This aspect allows a caretaker, for example, to be notified of the decision made by the symptom detection unit (121).

In an event prediction system (10) according to a sixth aspect, which may be implemented in conjunction with any one of the first to fifth aspects, the symptom detection unit (121) distinguishes one type of the particular event, for which the decision about the symptoms are to be made, from another.

This aspect enables not only detection of symptoms of the onset of a particular event but also distinction of one type of the particular event, for which the decision about the symptoms are to be made, from another. This facilitates analysis of the decision made by the symptom detection unit (121).

An event prediction method according to a seventh aspect includes: acquiring body movement data about a subject's body movement; and making, based on the body movement data, a decision about whether or not there are any symptoms of the onset of a particular event related to the subject.

This aspect allows for detecting, based on body movement data, symptoms of the onset of a particular event that could occur to the subject, i.e., a "sign" that appears before the particular event occurs. Thus, this event prediction method allows the user to detect event symptoms of the onset of the particular event related to the subject, which is one of advantages of this event prediction method.

A program according to an eighth aspect is designed to make a computer system execute the event prediction method according, to the seventh aspect.

This aspect allows for detecting, based on body movement data, symptoms of the onset of a particular event that could occur to the subject, i.e., a "sign" that appears before the particular event occurs. Thus, this program allows the user to detect event symptoms of the onset of the particular event related to the subject, which is one of advantages of this program.

Note that these aspects are only exemplary aspects of the present disclosure. That is to say, the present disclosure has many other aspects that have not been mentioned above. For example, various configurations of the event prediction system (10) according to the first and second embodiments and variations thereof may also be implemented as an event prediction method, a program for predicting an event, and a non-transitory storage medium that stores the program thereon.

Note that the configurations according to the second to sixth aspects are not essential constituent elements of the event prediction system (10) according to the first aspect but may be omitted as appropriate.

A sensor signal processing system (1) according to a ninth aspect includes an acquisition unit (13) and an acceleration calculation unit (111). The acquisition unit (13) acquires body movement data about a subject's body movement from a measuring device (2). The measuring device (2) outputs the body movement data. The acceleration calculation unit (111) calculates, based on the body movement data, acceleration of the subject's body movement.

This aspect allows acceleration of the subject's body movement to be calculated based on the body movement data acquired from the measuring device (2). According to the Newton's force equation (F=ma), force (F) is the product of acceleration (a) and mass (m). When the subject is conducting a physical activity using his or her whole body, the subject's weight corresponds to the mass. Supposing an increase or decrease in the subject's weight is negligible, the acceleration will correspond to the muscular strength that the subject exerted to conduct the physical activity. Thus, the acceleration obtained by the acceleration calculation unit (111) corresponds to the strength of the physical activity and the volume of the physical activity during a certain period is represented as the cumulative value of the acceleration during the certain period. Therefore, this sensor signal processing system (1) is allowed to evaluate the physical activity volume quantitatively by calculating the acceleration based on the body movement data, thus improving the accuracy of detection of the physical activity volume.

In a sensor signal processing system (1) according to a tenth aspect, which may be implemented in conjunction with the ninth aspect, the acceleration, calculation unit (111) calculates the acceleration by performing differentiation on multiple items, arranged time sequentially, of the body movement data.

This aspect allows the acceleration to be obtained by relatively simple calculation such as differentiation, thus lessening the processing load on the acceleration calculation unit (111).

In a sensor signal processing system (1) according to an eleventh aspect, which may be implemented in conjunction with the ninth or tenth aspect, the measuring device (2) includes a noncontact sensor (21) to detect the body movement data without making physical contact with the subject.

This aspect allows the acceleration to be obtained without interfering with the subject's movement for the purpose of acquiring the body movement data.

In a sensor signal processing system (1) according to a twelfth aspect, which may be implemented in conjunction with the eleventh aspect, the noncontact sensor (21) is a radio wave sensor to transmit and receive radio waves.

This aspect allows even subtle movements of the subject to be detected by the noncontact sensor (21), thus further improving the accuracy of detection of the physical activity volume.

In a sensor signal processing system (1) according to a thirteenth aspect, which may be implemented in conjunction with the twelfth aspect, the measuring device (2) compares a frequency of a radio wave received by the noncontact sensor (21) with a frequency of the radio wave transmitted by the noncontact sensor (21) to obtain a movement velocity of the subject.

This aspect allows the measuring device (2) to obtain the subject's movement velocity, thus enabling the sensor signal processing system (1) to calculate the acceleration by relatively simple processing.

A sensor signal processing system (1) according to a fourteenth aspect, which may be implemented in conjunction with any one of the ninth to thirteenth aspects, further includes an output unit (15). The output unit (15) outputs a result of calculation made by the acceleration calculation unit (111).

This aspect allows a caretaker, for example, to be notified of the result of calculation made by the acceleration calculation unit (111).

A sensor signal processing method according to a fifteenth aspect includes: acquiring body movement data about a subject's body movement from a measuring device (2) that outputs the body movement data; and calculating, based on the body movement data, acceleration of the subject's body movement.

This aspect allows acceleration of the subject's body movement to be calculated based on the body movement data acquired from the measuring device (2). According to the Newton's force equation (F=ma), force (F) is the product of acceleration (a) and mass (m). When the subject is conducting a physical activity using his or her whole body, the subject's weight corresponds to the mass. Supposing an increase or decrease in the subject's weight is negligible, the acceleration will correspond to the muscular strength that the subject exerted to conduct the physical activity. Thus, the acceleration obtained by acceleration calculating processing corresponds to the strength of the physical activity and the volume of the physical activity during a certain period is represented as the cumulative value of the acceleration during the certain period. Therefore, this sensor signal processing method allows the physical activity volume to be evaluated quantitatively by calculating the acceleration based on the body movement data, thus improving the accuracy of detection of the physical activity volume.

A program according to a sixteenth aspect is designed to make a computer system execute the sensor signal processing method of the fifteenth aspect.

This aspect allows acceleration of the subjects body movement to be calculated based on the body movement data acquired from the measuring device (2). According to the Newton's force equation (F=ma), force (F) is the product of acceleration (a) and mass (m). When the subject is conducting a physical activity using his or her whole body, the subject's weight corresponds to the mass. Supposing an increase or decrease in the subject's weight is negligible, the acceleration will correspond to the muscular strength that the subject exerted to conduct the physical activity. Thus, the acceleration obtained by acceleration calculating processing corresponds to the strength of the physical activity and the volume of the physical activity during a certain period is represented as the cumulative value of the acceleration during the certain period. Therefore, this program allows the physical activity volume to be evaluated quantitatively by calculating the acceleration based on the body movement data, thus improving the accuracy of detection of the physical activity volume.

Note that these aspects are only exemplary aspects of the present disclosure. That is to say, the present disclosure has many other aspects that have not been mentioned above. For example, various configurations of the sensor signal processing system (1) according to the first and second embodiments and variations thereof may also be implemented as a sensor signal processing method, a program, and a non-transitory storage medium that stores the program thereon.

Note that the configurations according to the tenth to fourteenth aspects are not essential constituent elements for the sensor signal processing system (1) according to the ninth aspect but may be omitted as appropriate.

The invention claimed is:

1. An event prediction system comprising:
    an acquisition unit configured to acquire body movement data about a subject's body movement from a measuring device configured to output the body movement data;
    a symptom detection unit configured to make, based on a subset, acquired during a past reference period, of the body movement data, a decision about whether or not there are any symptoms of an onset of a particular event related to the subject; and a presence detection unit configured to make, based on the body movement data, a decision about whether the subject is present in, or absent from, an object space, the presence detection unit being configured to determine, when a coefficient of an analysis model obtained by a time series analysis processing is greater than a predetermined threshold value or when a magnitude of the body movement data is greater than a predetermined decision value, that the subject is present in the object space.

2. The event prediction system of claim 1, further comprising an acceleration calculation unit configured to calculate, based on the body movement data, acceleration of the subject's body movement, wherein the symptom detection unit is configured to make the decision about the symptoms in accordance with a variation, obtained based on the body movement data, in volume of the subject's physical activity.

3. The event prediction system of claim 2, wherein the acceleration calculation unit is configured to calculate the acceleration by performing differentiation on multiple items, arranged time sequentially, of the body movement data.

4. The event prediction system of claim 2, further comprising an output unit configured to output a result of calculation made by the acceleration calculation unit.

5. The event prediction system of claim 1, further comprising an output unit configured to output the decision made by the symptom detection unit.

6. The event prediction system of claim 1, wherein the measuring device includes a noncontact sensor configured to detect the body movement data without making physical contact with the subject.

7. The event prediction system of claim 6, wherein the noncontact sensor is a radio wave sensor configured to transmit and receive radio waves.

8. The event prediction system of claim 7, wherein the measuring device is configured to compare a frequency of a radio wave received by the noncontact sensor with a frequency of the radio wave transmitted by the noncontact sensor to obtain a movement velocity of the subject.

9. The event prediction system of claim 1, wherein the symptom detection unit is configured to distinguish one type of the particular event, for which the decision about the symptoms is to be made, from another.

10. A sensor signal processing system comprising:

an acquisition unit configured to acquire body movement data about a subject's body movement from a measuring device configured to output the body movement data;

an acceleration calculation unit configured to calculate, based on the body movement data, acceleration of the subject's body movement; and a presence detection unit configured to make, based on the body movement data, a decision about whether the subject is present in, or absent from, an object space, the presence detection unit being configured to determine, when a coefficient of an analysis model obtained by a time series analysis processing is greater than a predetermined threshold value or when a magnitude of the body movement data is greater than a predetermined decision value, that the subject is present in the object space.

11. An event prediction method comprising:

acquiring body movement data about a subject's body movement from a measuring device configured to output the body movement data;

making, based on a subset, acquired during a past reference period, of the body movement data, a decision about whether or not there are any symptoms of an onset of a particular event related to the subject, making, based on the body movement data, a decision about whether the subject is present in, or absent from, an object space, in the step of making the decision, determining, when a coefficient of an analysis model obtained by a time series analysis processing is greater than a predetermined threshold value or when a magnitude of the body movement data is greater than a predetermined decision value, that the subject is present in the object space.

12. A non-transitory storage medium storing a program designed to make a computer system execute the event prediction method of claim 11.

* * * * *